United States Patent [19]
Fernandes

[11] Patent Number: 5,603,616
[45] Date of Patent: Feb. 18, 1997

[54] DENTISTRY IMPLANT METHOD

[76] Inventor: Americo Fernandes, 2055 McPhillips St., Winnipeg, Manitoba, Canada, R2V-3C6

[21] Appl. No.: 405,715

[22] Filed: Mar. 17, 1995

Related U.S. Application Data

[62] Division of Ser. No. 165,984, Dec. 13, 1993, Pat. No. 5,427,526.

[51] Int. Cl.⁶ .................................................. A61C 8/00
[52] U.S. Cl. ...................... 433/175; 433/201.1; 433/214
[58] Field of Search ................................... 433/173, 174, 433/175, 201.1, 214

[56] References Cited

U.S. PATENT DOCUMENTS

| | | | |
|---|---|---|---|
| 2,210,424 | 8/1940 | Morrison | 433/175 |
| 3,628,248 | 12/1971 | Kroder | 433/201.1 |
| 3,717,932 | 2/1973 | Brainin | 433/175 |
| 3,919,773 | 11/1975 | Freeman | 433/201.1 |
| 4,187,608 | 2/1980 | Nyce | 433/201.1 |
| 5,004,422 | 4/1991 | Propper | 433/175 |

FOREIGN PATENT DOCUMENTS 8201989  6/1982  WIPO ................................. 433/175

*Primary Examiner*—Cary E. O'Connor

[57] ABSTRACT

A dental implant that is either pre-formed having a general conical taper to reflect the average taper of a single rooted tooth, or custom manufactured to reflect a major portion of the root structure of a tooth that has been extracted. A plurality of retention elements are arranged on the distal half of the implant to provide immediate macro retention of the implant in the alveolar bone. The retention elements are tapered both longitudinally and circumferentially and can be biased relative to the longitudinal axis of the implant to provide a screw like mechanism when the implant is rotated in the alveolar bone. The retention elements are spaced about the implant surface to maximize stagger. This reduces the sheer forces generated on the alveolar bone during function and ensures that the implant remains tightly seated for an extended period of time. The custom implant impression method uses a thin impermeable membrane to line a recess in the alveolar bone prior to obtaining an impression to inhibit pieces of the impression material from entering the recess and surrounding area that may cause infections.

5 Claims, 3 Drawing Sheets

DENTISTRY IMPLANT METHOD

This application is a divisional application of U.S. Ser. No. 08/165,984 now U.S. Pat. No. 5,427,526.

FIELD OF THE INVENTION

This invention relates to the field of dental implants and to a method for preparing and custom dental implants.

BACKGROUND OF THE INVENTION

The natural teeth of a patient are often lost as a result of dental disease or trauma, making it desirable to replace a natural tooth with a prosthetic device. Treating with custom implants is ideal where the walls of the root are so thin that the problem tooth cannot be adequately treated with post and core, or in situations where the tooth has decayed to the point of involvement well below the crest of the alveolar bone. Dental arches that have short or long edentulous spaces, excellent bone quality, thickness and depth would be ideal situations where the treatment of choice is implants that are either preformed or custom made.

One type of prosthetic device is the dental endosteal implant that is intended to be surgically positioned into the bony structure (mandibular or maxillary alveolar bone), and be held there (a) by osseo-integration with the bony structure itself, (b) by ingrowth of fibrous tissue, (c) by the use of screws or self-retaining attachment mechanisms physically engaged to the bony structure, or (d) by any combination of the above. After healing the implant is fitted with a tooth-simulating prosthesis.

Since dental implants serve as the foundation for a dental prosthesis, implants must have sufficient mechanical strength and stability to withstand the forces and pressures generated during function (mastication etc.). The structural configuration of the implant and the manner in which it installed in the jawbone are determinants in the ability of the implant to maintain its installed position over an extended period of time.

More specifically, one of the common causes of failure of traditional implants is excessive loading on a small section of the alveolar bone due to the inadequate distribution of loading forces. It has been found that screw implants, for example, exert six times the force of normal teeth on the alveolar bone generated by average vertical masticular loads. As a result, over an extended period of time the increased pressure applied to the alveolar bone and surrounding area may result in the implant coming loose from the alveolar bone.

There are two main types of conventional implants: press-fit and threaded. Both types are installed into a prepared recess made in the alveolar bone.

The press-fitted implant lacks a macro retention mechanism, making it vulnerable to movement. As a result, there is a need to provide apertures in the implant to permit ingrowth of bony tissue to ensure a rigid attachment. However, the implant as installed can still be vulnerable to movement particularly if fibrous tissue growth exceeds the amount of alveolar bone growth throughout the apertures of the implant.

For example, U.S. Pat. No. 3,979,828 issued Sep. 14, 1976 to Taylor discloses an implant that has a configuration shaped to encourage hard tissue and bone growth into and through portions of the implant for increasing the mechanical interlock between the implant and the existing alveolar bone. Taylor states that a healing period is required to ensure that the required mechanical interlock is achieved. However, even after this healing period the implant can still become loose during function, since the only mechanical anchor is provided by bone and fibrous tissue growth that may be weak. This is primarily due to the fact that press-fit systems rely on strong bone growth to anchor the implant, and if fibrous tissue formation dominates the attachment to the implant then the implant can easily be loosened during function.

A variation of the press-fit type of implant is disclosed in U.S. Pat. No. 4,854,873 issued Aug. 8, 1989 to Linden. The Linden implant is installed by press fitting the rod type implant into a cylindrical hole and then twisting to anchor the implant in the alveolar bone. Linden discloses a cylindrical implant having a series of projecting plates that are arranged in circumferentially spaced longitudinal rows along quadrants of the cylindrical surface. Since the projecting plates have no flutes, and are radially aligned, there is no biasing movement of the implant in a longitudinal direction during the twisting operation.

Due to the longitudinal alignment of the Linden projecting plates, the implant provides limited resistance to dislodging the implant in an unseated direction (i.e. vertically in an extraction direction). In addition, cylindrical implants poorly distribute compressive forces and generate shears forces that may fragment and break the bone surrounding the implant during function.

The threaded type implant provides, at least initially, more stability than a press-fit attachment, but the implant is still vulnerable to movement and high levels of shear forces can be established between the implant and the alveolar bone during function. Consequently, it is usually necessary to rely on growth of new bone tissue and connective tissue to further stabilize the installed position of the implant.

For example, U.S. Pat. No. 3,849,887 issued on Nov. 26, 1974 to Brainin discloses an implant having a serrated or dentated surface section and one or more expanded grooves to provide temporary mechanical interlock during the early stages of the implantation process. With threaded implants the bone that grows between the flutes of the thread on the implant can be sheared away and fragmented due to the high levels of shear stress generated at these points during function.

This is a significant area of weakness for a threaded implant, since the implant has a tendency to loosen in the socket and therefore must be removed and replaced by a larger diameter implant.

The use of a conically tapered implant to distribute compressive forces evenly to surrounding alveolar bone has been proposed in the previously mentioned U.S. Pat. No. 3,979,828 (Taylor). However, more favourable force distribution would be obtained if the implant taper closely matches the recess in the alveolar bone after a single rooted tooth has been extracted.

A process for making custom implants is disclosed in Canadian Patent Application No. 2,029,646 laid-open on May 10, 1991 to Propper. Among many other steps, Propper disclosed the step of preparing a model of at least the major portion of the root of the extracted tooth. Propper teaches that conventional moulding practices are used, such as the lost-wax/wax-up process, for making a replica of at least part of the tooth.

The problem with this type of conventional moulding practice is that the impression material (typically rubber, silicone etc.) is in direct contact with the alveolar bone and surrounding tissue during the stage when an impression is being obtained. This can cause the impression material to seep into the surrounding tissue and cause adverse reactions such as infections etc.

Consequently, there is a need for an implant that:

(a) provides immediate macro retention without using continuous self-tapping threads, and does not rely solely on bone growth to stabilize the implant; and (b) minimizes sheer forces and maximizes the even distribution of compressive forces to the alveolar bone generated during function (mastication etc.).

In addition, there is a need for a safe method for obtaining a direct bone impression from a recess in the alveolar bone in order to manufacture a custom implant.

SUMMARY OF THE INVENTION

An object of the present invention is to provide a dental implant that is securely positioned in the alveolar bone immediately after placement, without the use of continuous self-tapping threads.

Another object of the present invention is to provide a dental implant that maximizes the even distribution of compressive forces generated during function.

Another object of the present invention is to provide a dental implant that minimizes sheer forces generated between the dental implant and the alveolar bone, thereby reducing the incidence of fragmentation of the alveolar bone.

Another object of the present invention is to provide a safe method for obtaining a impression from a recess in the alveolar one in order to manufacture a custom dental implant.

In accordance with one aspect of the invention there is provided a dental implant for insertion into an alveolar recess to form a root section, the dental implant comprising: a generally conical member having a longitudinal axis and an external surface tapering from a proximal end to a distal end, the surface generally corresponding to the recess; and two primary retention elements projecting from the surface of the member, the elements each having a longitudinal axis and a surface that tapers from a proximal end portion of the element to a distal end portion of the element, with the distal end portions of the elements being generally directed towards the distal end of the member; the two primary retention elements being spaced from each other in a circumferential direction about the member.

In accordance with another aspect of the invention there is provided a dental implant for insertion into an alveolar recess to form a root section, the dental implant comprising: a generally conical member having a longitudinal axis and an external surface tapering from a proximal end to a distal end, the surface generally corresponding to the recess; and two primary retention elements projecting from the surface of the member, the elements each having a longitudinal axis and a surface that tapers (i) from a proximal end portion of the element to a distal end portion of the element, and (ii) in a direction circumferentially around the surface of the implant, with the distal end portions of the elements being generally directed towards the distal end of the member; and (a) the two primary retention elements being substantially uniformly distributed around the surface of the member at different longitudinal positions on the surface of the member; and (b) the radial extent of the implant measured at the proximal end of each of the two primary retention elements being less than the radial extent at the proximal end of the member.

In accordance with another aspect of the invention there is provided a method of preparing a custom dental implant, comprising the following steps in the order recited: (a) extracting a tooth to leave a recess for later reception of the dental implant; (b) lining the recess with a thin flexible impermeable sheathing; (c) moulding an impression material into the recess lined with the thin flexible impermeable sheathing to obtain an impression of at least a major portion of the recess; and (d) preparing the custom dental implant from the impression obtained from step (c).

BRIEF DESCRIPTION OF THE DRAWINGS

Embodiments of the invention will be described by way of example in conjunction with the drawings in which.

DETAILED DESCRIPTION OF PREFERRED EMBODIMENTS OF THE INVENTION

Figure 1:
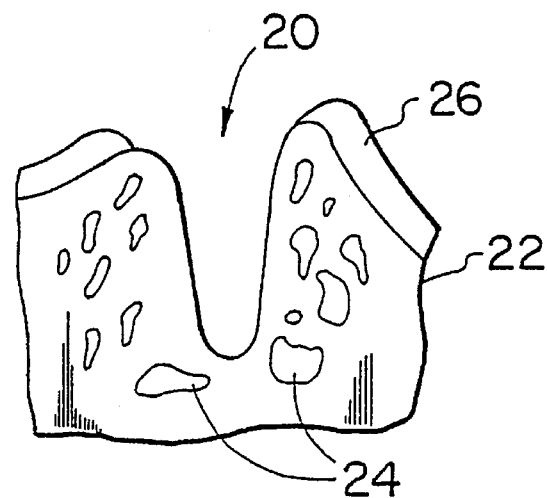
FIG. 1 shows a schematic representation of an alveolar bone after a natural tooth has been extracted.

FIG. 1 shows a recess 20 formed in a jaw bone portion 22 after a single rooted tooth (not shown) has been extracted and/or after preparation by a drill. The jaw bone portion 22 includes alveolar bone 24 and an alveolar ridge or gingiva 26.

Figure 2:
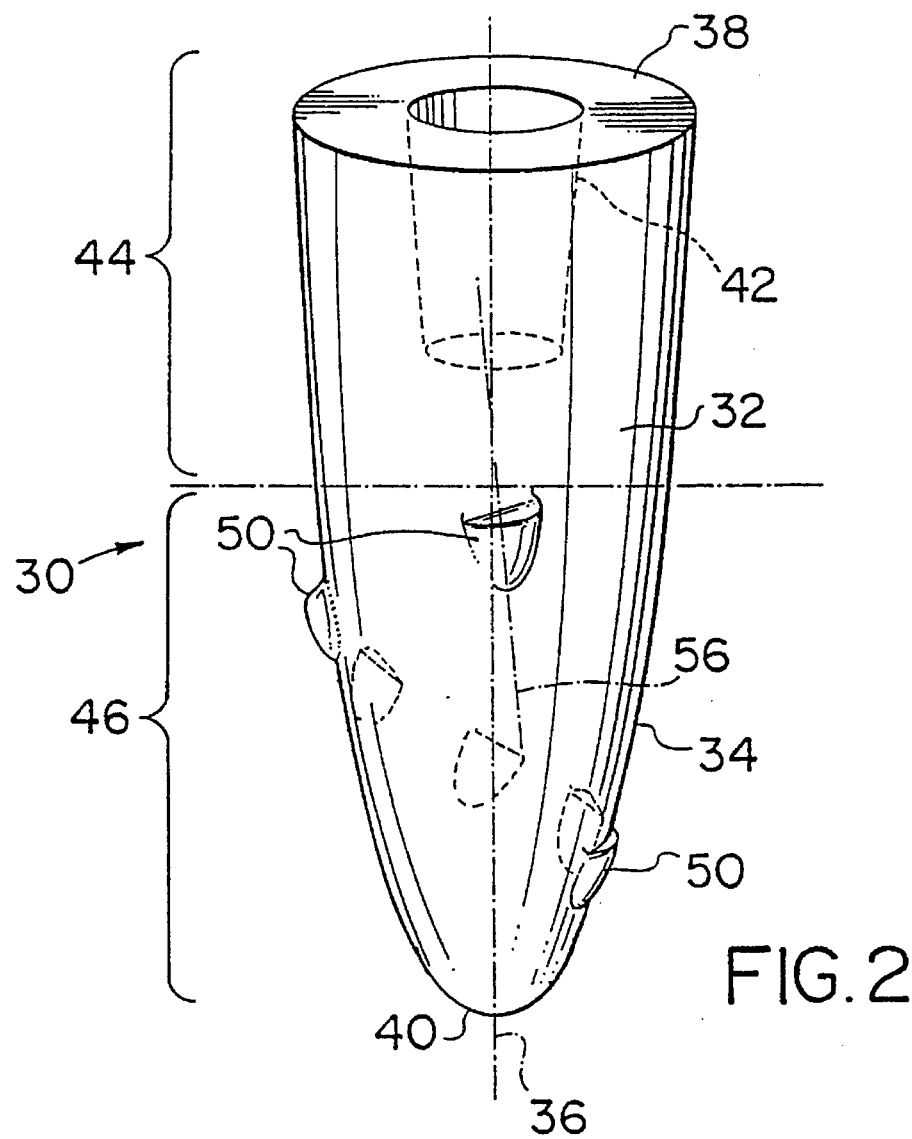
FIG. 2 shows a perspective view of a dental implant according to one embodiment of the invention.

A dental implant according to an embodiment of the invention is generally indicated by reference numeral 30 in FIG. 2.

The dental implant 30 includes a generally conical body member 32 having a longitudinal axis 36 and an external surface 34 tapering from a proximal end 38 to a rounded distal end 40. The body member 32 is formed of a biochemical material such as titanium.

A tapered abutment socket 42 is provided at the proximal end 38 for receiving an abutment (not shown), to which a tooth-simulating prosthesis (not shown) is to be mounted. The socket 42 is tapered to generally correspond to the taper of the surface 34 to ensure that masticular loads are evenly transmitted from the abutment to the body member 32 of the implant 30.

The body member 32 includes two main sections; a proximal half 44 (extending from the proximal end 38 to approximately the longitudinal midpoint of the member 32) and a distal or apical half 46 (extending from the distal end 40 to approximately the longitudinal midpoint of the member 32).

According to the aspect of the invention that uses preformed implants, the tapered surface 34 is designed to reflect the average taper from proximal to distal of a single rooted tooth. This will ensure that the alveolar bone 24 surrounding the implant 30 receives favourable force distribution necessary to its health.

In order to determine average tapers, over 100 single rooted teeth were examined. The diameter of each tooth was measured at the cemento-enamel junction (C.E.J.) and again at the widest point at 10 mm (0.394 in), 12 mm (0.472 in), and 15 mm (0.591 in) apical to the C.E.J., taking the longest path (convex) along the root surface. Taper factors were obtained by dividing the 10 mm (0.394 in), 12 mm (0.472 in), and 15 mm (0.591 in) diameter measurements by the C.E.J. value.

For example, the study found that the average taper factor at 10 mm (0.394 in) was 0.67 mm (0.026 in), 0.57 mm (0.022 in) at 12 mm (0.472 in), and 0.49 mm (0.019 in) at 15 mm (0.591 in) apically.

The tapered surface 34 of the body member 32 is provided with a plurality of retention elements 50 that project from the surface 34. At least two retention elements 50 must be spaced from each other in a circumferential direction about the member 32 for adequate macro retention of the implant 30 in the bone 24.

Figure 3:
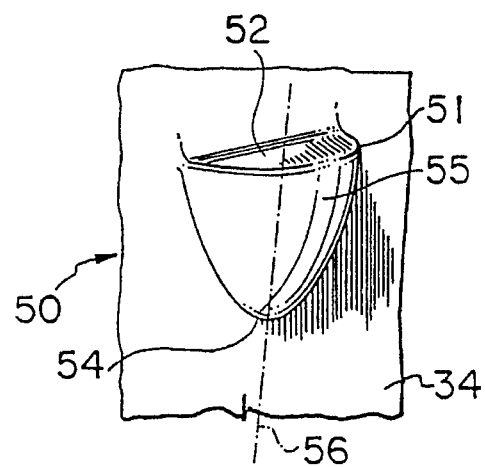
FIG. 3 shows a partial cut-away enlarged view of a portion of the dental implant illustrating one of the plurality of retention elements shown in FIG. 2.

Referring to FIG. 3, each retention element 50 is provided with a proximal end 51, having a proximal plateau 52, a rounded distal end 54 and a surface 55 that (a) tapers longitudinally along a longitudinal axis 56 from the proximal end 51 to the distal end 54, such that the surface 55 gradually tapers into the surface 34 of the member 32, and (b) tapers circumferentially, relative to the member 32, from one lateral edge of the retention element 50 to the other.

The proximal plateau 52 intersects the tapered surface 34 of the implant 30 at approximately 90 degrees to ensure that the elements 50 provide an adequate resistance to movement during masticular loading.

The degree of longitudinal taper of each retention element 50 generally corresponds to the average taper of single rooted teeth, as discussed in conjunction with the tapered surface 34 of implant 30. As a result, the retention elements 50 are tapered to approximately reflect the tapered surface 34 of the implant 30.

The circumferential taper of the retention element 50 results in a screw type bias of the retentive element 50 such that the implant 30 can be rotated into the recess 20 in the alveolar bone 24. More specifically, when the member 32 is rotated the retention elements 50 act on the alveolar bone 24 to move the member 32 in a longitudinal direction along the axis 36.

Each element 50 has a predefined longitudinal extent defined by the distance between its proximal end 51 and distal end 54 and a predefined circumferential extent defined by the distance between its lateral edges at the proximal end 51 of the element 50.

The circumferential and longitudinal extents of the elements 50 need not be identical. However, the circumferential extent of the elements 50 should range from approximately 5 degrees to approximately 45 degrees. More specifically, ideal retention would be obtained if the circumferential extent of the elements 50 range from approximately 10 degrees to approximately 20 degrees.

The retention elements 50 are rounded to reduce sharp acute configurations (recessions or angles) to reduce shear forces on the alveolar bone 24 and to avoid the problem of decreased vascularity resulting in fibrous healing (unwanted) instead of asseous healing, which is more desirable. Rounded edges will also minimize bone trauma and deliver better distribution of compressive forces to the bone 24.

The longitudinal axis 56 of the retention element 50 intersects the longitudinal axis 36 of the body member 32 (intersection shown in FIG. 2) at an angle that is less than 45 degrees. This orientation assists in allowing the implant 30 to be either press fit (with an ideal intersection angle of 0 degrees) or screwed (with an ideal intersection angle of between 3 and 12 degrees) into the recess 20 formed in the alveolar bone 24.

The retentive elements 50 are located at the distal or apical half 46 of the implant 30. This will ensure that the alveolar bone 24 will seal properly at the proximal half 44. In addition, the radial extent of the implant 30 measured at the proximal end 51 of each of the elements 50 is less than the radial extent at the proximal end 42 of the member 32.

This radial extent relationship effectively limits the radial projection of the elements 50 to ensure that there are no cuts in the bone 24 that are exposed at the proximal end 38 when the implant 30 has been placed to reduce the incidence of infection.

Figure 4:
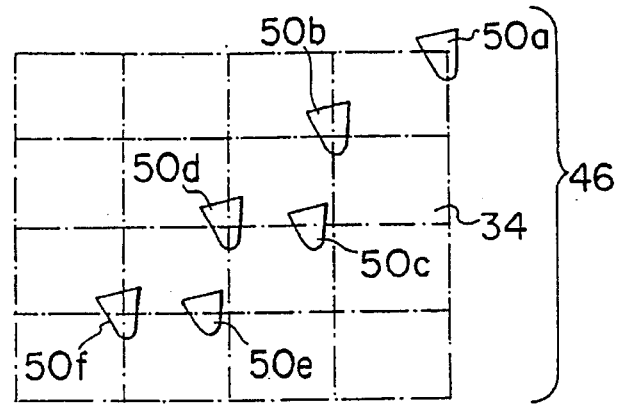
FIG. 4 shows a plan view of the distal half of the dental implant surface shown in FIG. 2 to illustrate the relative locations of the retention elements.

In the embodiment shown in FIG. 2, six retention elements 50 are uniformly distributed at a series of locations on the implant surface 34. Referring to FIG. 4, the retention elements 50 are arranged to optimize stagger. Specifically, element groups 50a; 50b,c; 50d,e; and 50f are located in approximately the four quadrants of the surface 34 of the implant 30.

At least two of the elements 50a–f, termed the primary retention elements (for example, 50a and 50f), are circumferentially separated by a distance at least as great as the larger of the circumferential extents of the two primary retention elements 50a, 50f. In addition, the two primary retention elements 50a and 50f are longitudinally separated a distance at least as great as the larger of the longitudinal extents of the two primary retention elements 50a, 50f. This spaced arrangement will minimize unwanted shear forces on the alveolar bone 24 during function.

The additional retention elements 50b, 50c, 50d, and 50e, are preferably similarly separated from at least one of the two primary retention elements 50a, 50f. Consequently, the arrangement of elements 50 can be quite random provided that at minimum the two primary retention elements 50a, 50f are circumferentially spaced about the surface 34 of the member 32.

Figure 5:
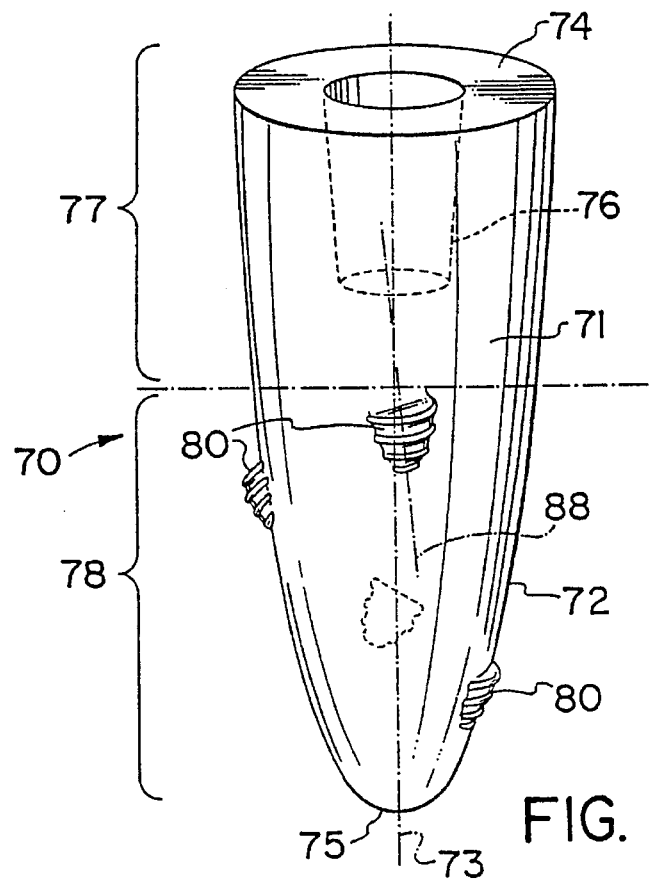
FIG. 5 shows a perspective view of a dental implant according to another embodiment of the invention.

A dental implant according to another embodiment of the invention is generally indicated by reference numeral 70 in FIG. 5.

The dental implant 70 includes a generally conical body member 71 having a longitudinal axis 73 and an external surface 72 tapering from a proximal end 74 to a rounded distal end 75.

A tapered abutment socket 76 is also provided at the proximal end 74 for receiving an abutment (not shown) as described in conjunction with the implant 30.

The body member 71 includes two main sections; a proximal half 77 (extending from the proximal end 74 to approximately the longitudinal midpoint of the member 71) and a distal or apical half 78 (extending from the distal end 75 to approximately the longitudinal midpoint of the member 71).

According to the aspect of the invention that uses preformed implants, the tapered surface 72 is designed to reflect the average taper from proximal to distal of a single rooted tooth. This will ensure that the alveolar bone 24 surrounding the implant 70 receives favourable force distribution necessary to its health. The degree of taper of the surface 72 is similar to surface 34 as described in conjunction with implant 30.

The tapered surface 72 of the body member 71 is provided with a plurality of retention elements 80 that project from the surface 72. At least two retention elements 80 must be spaced from each other in a circumferential direction about the member 71 for adequate macro retention of the implant 70 in the bone 24.

Figure 6:
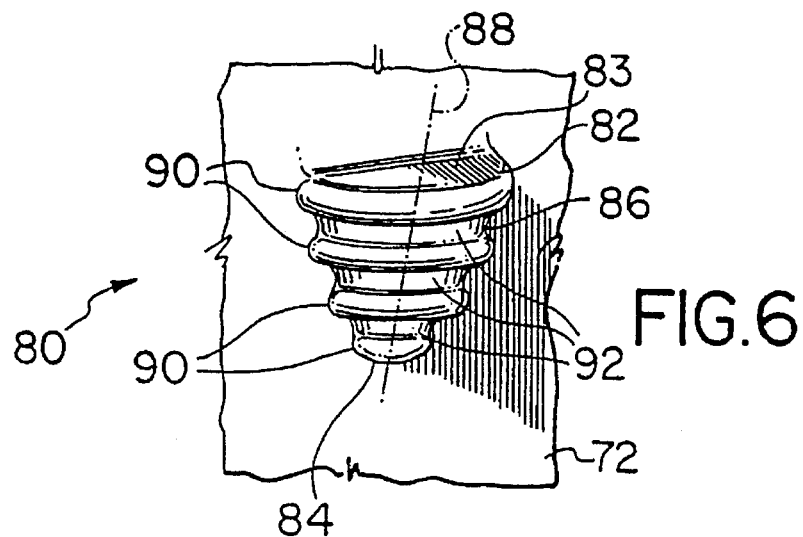
FIG. 6 shows an enlarged view of a portion of the dental implant illustrating one of the plurality of retention elements shown in FIG. 5.

Referring to FIG. 6, each retention element 80 is provided with a proximal end 82, having a proximal plateau 83, a distal end 84 and a surface 86 that (a) generally tapers longitudinally along a longitudinal axis 88 from the proximal end 82 to the distal end 84, such that the surface 86 gradually tapers into the surface 72 of the member 71, and (b) tapers circumferentially, relative to the member 71, from one lateral edge of the element 80 to the other.

The proximal plateau 83 intersects the tapered surface 72 of the implant 70 at approximately 90 degrees to ensure that the elements 80 provide an adequate resistance to movement during masticular loading.

The retention element 80 includes a series of rounded ribs 90 and channels 92 that follow the same direction of the proximal plateau 83 of the retention element 80.

The degree of longitudinal taper of each retention element 80 generally corresponds to the average taper of single rooted teeth, as described in conjunction with the taper of the retention element 50. As a result, the retention elements 80 are tapered to approximately reflect the tapered surface 72 of the implant 70.

The circumferential taper of the elements 80 as well as the ribs 90 and channels 92 result in a screw type of the retentive element 80 such that the implant 70 can be rotated into the recess 20 in the alveolar bone 24.

Each element 80 has a predefined longitudinal extent defined by the distance between its proximal end 82 and distal end 84 and a predefined circumferential extent defined by the distance between its lateral edges at the proximal end 82 of the element 80.

The circumferential and longitudinal extents of the elements 80 need not be identical. However, the circumferential extent of the elements 80 should range from approximately 5 degrees to approximately 45 degrees. More specifically, ideal retention would be obtained if the circumferential extent of the elements 80 range from approximately 10 degrees to approximately 20 degrees.

The retention elements 80 as a whole as well as the ribs 90 and channels 92 specifically are rounded to reduce sharp acute configurations (recessions or angles) to reduce shear forces on the alveolar bone 24 and to avoid the problem of decreased vascularity resulting in fibrous healing (unwanted) instead of asseous healing, which is more desirable. Rounded edges will also minimize bone trauma and deliver better compressive forces to the bone 24.

The longitudinal axis 88 of the retention element 80 intersects the longitudinal axis 73 of the body member 71 (intersection shown in FIG. 5) at an angle that is less than 45 degrees. This orientation assists in allowing the implant 70 to be either press fit (with an ideal intersection angle of 0 degrees) or screwed (with an ideal intersection angle of between 3 and 12 degrees) into the recess 20 formed in the alveolar bone 24.

The retentive elements 80 are located at the distal or apical half 78 of the implant 70. This will ensure that the alveolar bone 24 will seal properly at the proximal half 77. In addition, the radial extent of the implant 70 measured at the proximal end 82 of each of the elements 80 is less than the radial extent at the proximal end 74 of the member 71.

This radial extent relationship effectively limits the radial projection of the elements 80 to ensure that there are no cuts n the bone 24 that are exposed at the proximal end 74 when the implant 70 has been placed to reduce the incidence of infection.

Figure 7:
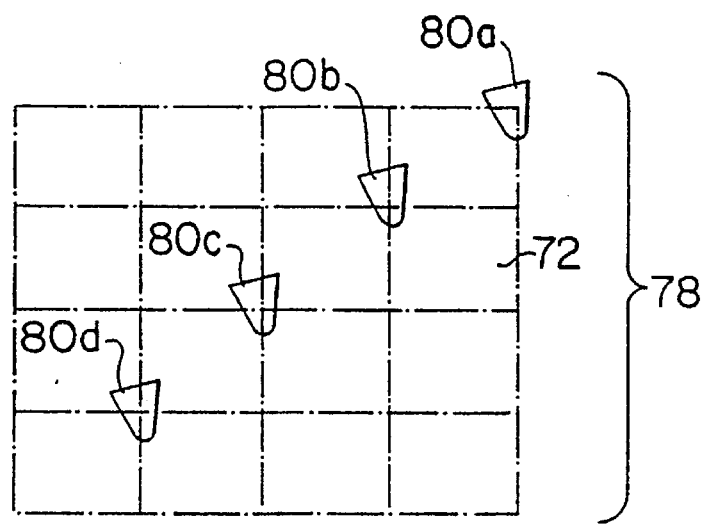
FIG. 7 shows a plan view of the distal half of the dental implant surface shown in FIG. 5 to illustrate the relative locations of the retention elements.

In the embodiment shown in FIG. 5, four retention elements 80 are uniformly distributed at a series of locations on the implant surface 72. Referring to FIG. 7, the retention elements 80 are arranged to optimize stagger.

Specifically, elements 80a; 80b; 80c; and 80d are located in approximately the four quadrants (i.e. spaced circumferentially by 90 degrees) of the surface 72 of the implant 70.

At least two of the elements 80a–d, termed the primary retention elements (for example, 80a and 80d ), are circumferentially separated by a distance at least as great as the larger of the circumferential extents of the two primary retention elements 80a, 80d. In addition, the two primary retention elements 80a and 80d are longitudinally separated by a distance at least as great as the larger of the longitudinal extents of the two primary retention elements 80a, 80d. This spaced arrangement will minimize unwanted shear forces on the alveolar bone 24 during function.

The additional retention elements 80b, and 80c are preferably similarly separated from at least one of the two primary retention elements 80a, 80d. Consequently, the arrangement of elements 80 can be quite random provided that at minimum the two primary retention elements 80a, 80d are circumferentially spaced about the surface 72 of the member 71.

To install the implant 30, 70 into the recess 20 the member 32, 71 is twisted or pressed into the recess 20. Depending on the orientation of the retention elements 50, 80, upon twisting the implant 30, 70 there will be a downward (or upward) longitudinal movement of the implant 30, 70 into (or out of) the recess 20. The proximal ends 52, 82 undercut the bone to provide a very secure immediate retention of the implant 30, 70.

After a healing period, generally six months, the alveolar bone 24 will grow around the implant 30, 70 and the retention elements 50, 80 to provide a very securely positioned implant. The implant 30, 70 maximizes the distribution of compressive forces generated during function based on its generally conically tapered configuration, which is very important to the health of the alveolar bone 24.

In addition, the shape, orientation and arrangement of the retention elements 50, 80 makes the implant highly resistance to dislodging forces and significantly reduces sheer forces acting to the surrounding alveolar bone 24.

As previously discussed, it is desirable that the implant 30, 70 have a taper that reflects the taper of the root of an average single rooted tooth. However, the implant 30, 70 could also be custom manufactured by making an actual impression of the recess 20 in the alveolar bone 24 where the defective tooth has been removed.

Custom manufacturing of the implant 30, 70 allows the dentist to treat many possible situations by being able to create a unique infinite array of implant possibilities. In the case of using custom implants the shape, of course, will not be as uniformly conical as shown in FIGS. 2 and 5 and as a result the implant may only be able to be press fitted into the recess 20. However, the shape will be generally conical with a slightly curved longitudinal axis to reflect the shape of a single rooted tooth.

Figures 8A, 8B:
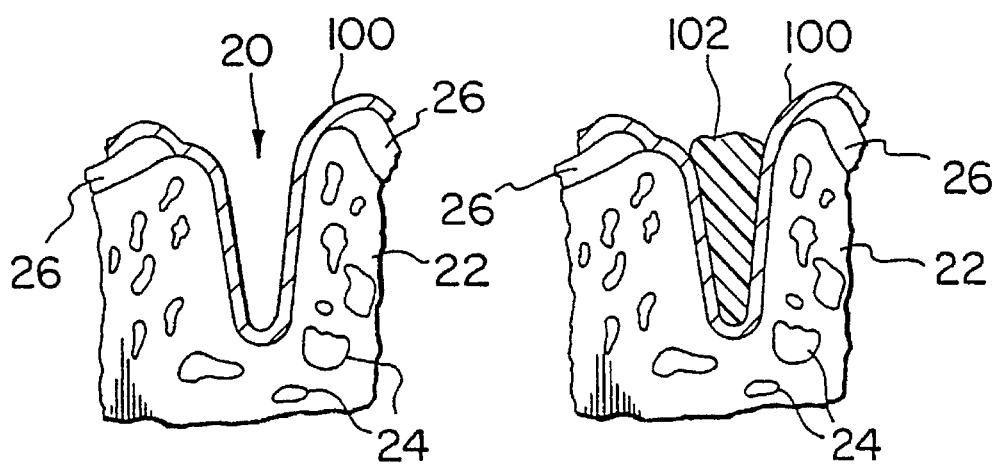
FIG. 8A shows the alveolar bone after a natural tooth has been extracted in which a impermeable sheath is placed according to the method of the present invention.
FIG. 8B shows the alveolar bone arrangement of FIG. 8A in which impression material is placed in the recess according to the method of the present invention.

Referring to FIGS. 8A and 8B, the method of preparing and placing the custom implant of the present invention involves the following steps:

(a) extract the tooth to reveal the recess 20 in the alveolar bone 24, or create a unique recess with a drill;

(b) line the recess 20 with a thin flexible impermeable sheathing 100 such as plastic sheathing;

(c) prepare an impression of at least a major portion of the recess 20 by moulding an impression material 102, for example, silicone, rubber base alginate, wax etc., containing radio-opaquers into the recess 20 lined with the sheathing 100; the use of the sheathing 100 inhibits the retention of the impression material 102 within the bone 24 and the surrounding tissue;

(d) as an optional step, a radiograph can be taken after the impression is made to check if pieces of the impression material have been left behind;

(e) mark the bone level to indicate the crestal bone level;

(f) to ensure a tight and retentive fit, the implant impression is painted with spacer (any film, paint etc. compatible with the alveolar bone 24 and the implant 30, 70), adding approximately 0.5 mm to the overall dimension of the implant;

(g) from the impression prepared, manufacture an implant comprising a replica of the model, including an arrangement of retention elements 50, 80 according to the present invention;

(h) the extraction recess is emptied and bleeding is established with a curette;

(i) the implant is tapped (if the shape of the custom implant is a slightly irregular conical shape, to reflect the root of an actual tooth) or screwed (if the shape of the custom implant is generally a regular conical shape, as shown in FIGS. 2 and 5) into place encountering mild resistance at level of it being two-thirds seated; it is preferable to seat the implant 1–2 mm below the crest of the alveolar bone to enhance soft tissue coverage; the surface of the implant is in contact with a substantial area of the recess wall; and (j) after approximately 6 months, if osseo-integration has occurred, the root implant is ready to be restored with an abutment and prosthetic tooth.

The present invention provides either a pre-formed dental implant that has a generally conical shape to reflect the average taper of single rooted teeth, or a custom fabricated dental implant, manufactured based on an impression made from a recess in an alveolar bone according to the method described. Both types of implants, pre-formed or custom, are provided with retention elements arranged according to the invention as described.

As a result, each type of implant (a) can be securely positioned in the alveolar bone, without the use of continuous self-tapping threads, (b) maximizes the even distribution of compressive forces generated during function, and (c) minimizes sheer forces generated between the implant and the alveolar bone.

Although the various aspects of the present invention have been discussed in conjunction with dentistry, the applications for implants (pre-formed, and custom) can be readily adapted to other medical areas, such as orthopaedics.

I claim:

1. A method of preparing a custom dental implant, comprising the following steps in the order recited:

(a) extracting a tooth to leave a recess for later reception of the dental implant;

(b) lining the recess with a thin flexible impermeable sheathing;

(c) moulding an impression material into the recess lined with the thin flexible impermeable sheathing to obtain an impression of at least a major portion of the recess; and (d) preparing the custom dental implant from the impression obtained from step (c).

2. The method of claim wherein at step (c) radio-opaquers are added to the impression material.

3. The method of claim 2, further comprising the step of taking a radiograph of the recess and a surrounding region to ensure that no impression material remains after the impression containing radio-opaquers has been obtained.

4. The method of claim 1, further comprising the step of painting the impression obtained from step (c) with a spacer material to increase the overall dimension of the impression.

5. The method of claim 4, wherein the spacer material increases the overall dimension of the impression by approximately 0.5 mm.

* * * * *